(12) United States Patent
Koike et al.

(10) Patent No.: US 9,770,389 B2
(45) Date of Patent: Sep. 26, 2017

(54) MEDICINE DISPENSING DEVICE

(71) Applicant: YUYAMA MFG. CO., LTD., Toyonaka-shi, Osaka (JP)

(72) Inventors: Naoki Koike, Toyonaka (JP); Masao Fukada, Toyonaka (JP)

(73) Assignee: YUYAMA MFG. CO., LTD., Toyonaka-shi (JP)

( * ) Notice: Subject to any disclaimer, the term of this patent is extended or adjusted under 35 U.S.C. 154(b) by 0 days.

(21) Appl. No.: 15/030,820

(22) PCT Filed: Oct. 15, 2015

(86) PCT No.: PCT/JP2015/079189
§ 371 (c)(1),
(2) Date: Apr. 20, 2016

(87) PCT Pub. No.: WO2016/067929
PCT Pub. Date: May 6, 2016

(65) Prior Publication Data
US 2016/0331640 A1 Nov. 17, 2016

(30) Foreign Application Priority Data
Oct. 31, 2014 (JP) .................................. 2014-222313

(51) Int. Cl.
*G06F 19/00* (2011.01)
*A61J 3/00* (2006.01)
(Continued)

(52) U.S. Cl.
CPC . *A61J 3/00* (2013.01); *A61J 1/03* (2013.01); *A61J 7/0084* (2013.01); *A61J 7/0463* (2015.05); *G06F 19/3456* (2013.01)

(58) Field of Classification Search
CPC . G07F 17/0092; B65B 5/103; G06F 19/3456; G06F 19/3462
(Continued)

(56) References Cited

U.S. PATENT DOCUMENTS 5,713,487 A * 2/1998 Coughlin ............. G06Q 20/342
221/2
6,535,637 B1 * 3/2003 Wootton ................. B65B 57/00
221/102
(Continued)

FOREIGN PATENT DOCUMENTS

JP 2012-130779 A 7/2012
JP 2013-226182 A 11/2013
(Continued)

OTHER PUBLICATIONS

ISA/JP, International Search Report issued on Nov. 10, 2015, International Application No. PCT/JP2015/079189 Total 3 pages with English translation.

*Primary Examiner* — Timothy Waggoner
(74) *Attorney, Agent, or Firm* — Masuvalley & Partners

(57) ABSTRACT

Systems and methods for preventing a container from being replenished with the wrong medicine are described. This is achieved by the following process: first, a user places a container on a placement unit and reads a symbol attached to a bottle. Then, a determination is made so as to whether the medicine in the bottle is the correct medicine. If the medicine is incorrect, a message indicating the medicine is incorrect is displayed. If the medicine is correct, a camera records video of the medicine replenishment operation. Once the medicine replenishment is completed, a photographed image of the medicine inside the container and an image of the correct medicine for replenishing the container are displayed. Then, the user views these images and confirms whether the medicine used to replenish the container (Continued)

was correct. If this confirmation is not completed, the medicine dispensing device will not dispense medicine from the container.

14 Claims, 11 Drawing Sheets

(51) Int. Cl.
*A61J 1/03* (2006.01)
*A61J 7/00* (2006.01)
*A61J 7/04* (2006.01)

(58) Field of Classification Search
USPC .................................................. 700/231–244
See application file for complete search history.

(56) References Cited

U.S. PATENT DOCUMENTS

| | | | | |
|---|---|---|---|---|
| 6,711,460 B1* | 3/2004 | Reese | ................ | G06F 19/3456 700/216 |
| 6,771,369 B2* | 8/2004 | Rzasa | ................ | G01J 3/02 250/339.07 |
| 7,014,063 B2* | 3/2006 | Shows | ................ | G06F 19/3462 221/211 |
| 7,840,307 B2* | 11/2010 | Mauger | ................ | G07F 11/62 700/231 |
| 7,918,068 B2* | 4/2011 | Kumano | ................ | G07F 17/0092 221/9 |
| 7,930,064 B2* | 4/2011 | Popovich, Jr. | ................ | G07F 17/0092 221/2 |
| 7,995,831 B2* | 8/2011 | Eller | ................ | G06F 19/327 382/142 |
| 8,141,330 B2* | 3/2012 | Henkel | ................ | B65B 5/103 53/237 |
| 8,521,326 B1* | 8/2013 | Holtje | ................ | G07F 17/0092 221/103 |
| 2011/0170655 A1* | 7/2011 | Yuyama | ................ | G07F 11/66 377/6 |

FOREIGN PATENT DOCUMENTS

WO      2010/110360 A1    9/2010
WO      2011/067897 A1    6/2011

* cited by examiner

MEDICINE DISPENSING DEVICE

This application is the U.S. National Phase of International Application No. PCT/JP2015/079189 filed on Oct. 15, 2015, and claims priority under 35 U.S.C. §119 to Japanese Patent Application No. 2014-222313, filed on Oct. 31, 2014, which are hereby expressly incorporated by reference in their entirety for all purposes.

TECHNICAL FIELD

The present invention relates to a medicine dispensing device for dispensing medicine stored in a container.

BACKGROUND OF THE DISCLOSURE

Medicine dispensing devices which automatically dispense a prescribed quantity of a prescribed medicine based on a prescription are known. For example, the applicants of the present application developed a medicine dispensing device as described above in patent document 1: International Publication Application No. 2010/110360. This medicine dispensing device has received favorable reviews, and has received favorable ratings from pharmacists for its ability to make the operation of preparing prescriptions more efficient.

With this medicine dispensing device, each type of medicine that is dispensed is stored in a plurality of cassettes. In case the medicine cassette runs short of medicine after dispensing medicine, the pharmacist retrieves the cassette from the device, and manually replenishes the cassette with medicine. While performing this task, there is always a possibility of occurring human errors in that the cassette is replenished with the wrong medicine.

An object of the present invention is to prevent a container, which stores medicine and is provided with a medicine dispensing device, from being replenished with the wrong medicine.

SUMMARY OF THE INVENTION

In accordance with one aspect of the present invention, there is provided a medicine dispensing device. The medicine dispensing device includes a container, a camera, an optical scanner, and a display device. The container stores medicines to be dispensed by the medicine dispensing device, and in normal conditions, the container is preferably arranged by a container arrangement unit provided with the medicine dispensing device. Furthermore, the medicine dispensing device is preferably configured such that only one single container can be retrieved at a time from the container arrangement unit. The camera is capable of photographing medicine inside the container, and is preferably capable of filming video.

When the container is replenished with medicines, first, the optical scanner scans a symbol attached to a bottle in which medicine is stored. Next, the medicine dispensing device determines whether or not the medicine stored in the bottle is the correct medicine for replenishing the container based on information obtained from the scanned bottle. If the medicine stored in the bottle is not the correct medicine for replenishing the container, the medicine dispensing device sends a notification indicating that the medicine is not correct. On the other hand, if the medicine stored in the bottle is the correct medicine for replenishing the container, the user replenishes the container with the medicine in the bottle. At this time, the camera preferably records video of the replenishing operation of container with this medicine. Furthermore, after the container is replenished with medicine, the camera photographs the replenished medicine inside the container.

In the next step, the medicine dispensing device displays the image of the medicine photographed by the camera on the display device. Prior to this, the medicine dispensing device preferably acquires an image prepared in advance of the medicine that should be used to replenish the container. Furthermore, the medicine dispensing device also preferably displays on the display device the image of medicine photographed by the camera and the acquired medicine image prepared in advance. Next, the user confirms whether or not the medicine replenished in the container is the correct medicine based on the images of the medicine displayed on the display device. If the user determines that the medicine is correct, the medicine dispensing device receives an input from the user confirming that the medicine photographed in the image is the correct medicine for replenishing the container. Until this confirmation input is received, the medicine dispensing device does not dispense medicine from the container replenished with medicine. Lastly, the user preferably returns the container replenished with medicine to the container arrangement unit.

In accordance with a second aspect of the present invention, there is provided a medicine dispensing device. The medicine dispensing device includes a container, a lock release device, and an optical scanner. The container stores medicine to be dispensed by the medicine dispensing device. Moreover, the container is capable of opening and closing, and being locked in the closed state. Furthermore, the container is preferably provided with a memory medium capable of specifying medicine to be stored by the container. The lock release device releases the lock of the container. The container also preferably has a lid capable of opening and closing, and the lock release device is preferably configured so as to cancel the lock of the lid of the container.

The medicine dispensing device further preferably includes a camera and a display device. The camera is capable of photographing medicine inside the container. Furthermore, the camera is also preferably capable of recording videos. The medicine dispensing device also preferably has a container arrangement unit, and a placement unit, where a plurality of containers are arranged within the container arrangement unit. Furthermore, replenishment of the medicine into the container is preferably performed by the placement unit.

When the container is to be replenished with medicine, first, the container to be replenished with medicine is moved from the container arrangement unit to the placement unit. In a preferred embodiment, the medicine dispensing device acquires information stored in the memory medium provided with the container, and then specifies the medicine stored in the container based on that information. Furthermore, the optical scanner scans a symbol attached to a bottle in which medicine is stored, and through this, the medicine dispensing device obtains information relating to medicine stored in the bottle. Next, the medicine dispensing device determines whether or not the medicine stored in the bottle is the correct medicine for replenishing the container based on information of medicine acquired from the scanned bottle.

In the preferred embodiment, the medicine dispensing device compares information of medicine to be stored in the container, obtained from the memory medium provided with the container, with information of medicine obtained from the scanned bottle, and thereby determines whether the medicine stored in the bottle is the correct medicine for replenishing the container. If the medicine dispensing device determines that the medicine thereof is the correct medicine, the medicine dispensing device drives the lock release device so that the lock release device releases the lock of the container. In this preferred embodiment, the lock release device releases the lock of the lid of the container moved to the placement unit. After the lock is being released, the camera preferably takes video of the replenishing operation of container with this medicine.

If the lock of the container is being released, the user replenishes the container with the medicine in the bottle. Once replenishment of the container with the medicine has been completed, the camera preferably photographs the medicine replenished inside the container. Furthermore, the medicine dispensing device preferably obtains an image prepared in advance of medicine based on information of the medicine obtained from the scanned bottle prior to replenishing the medicine. Furthermore, the medicine dispensing device displays an image of medicine inside the container photographed by the camera after the medicine has been replenished, and an image prepared in advance of the medicine on the display device. Lastly, the user views both images, and confirms whether or not the medicine replenished in the container is the correct medicine for replenishment, and the medicine dispensing device preferably receives an input from the user indicating to the effect that the replenished medicine is correct.

In accordance with a third aspect of the present invention, there is provided a medicine dispensing device. The medicine dispensing device may include a container, an opening and closing device, a medicine insertion device, and an optical scanner. The container stores medicine to be dispensed by the medicine dispensing device and is also capable of being opened and closed. Furthermore, the container is preferably capable of locking in a closed state. The opening and closing device opens and closes the container, and the medicine insertion device inserts medicine into the container. This medicine insertion device preferably has a gripping device for gripping a bottle in which medicine is stored.

In a preferred embodiment, the medicine dispensing device may further include a rotation device, a lock release device, a camera, and a display device. The rotation device rotates a bottle in which medicine is stored. The camera is capable of photographing medicine inside the container, and the lock release device releases the lock of the container. Furthermore, the medicine dispensing device preferably has a container placement unit and a bottle placement unit. When a container is to be replenished with medicine, the container into which medicine will be replenished is placed at the container placement unit, and a bottle storing medicine for replenishment is placed at the bottle placement unit. The container placement unit and the bottle placement unit are preferably installed at mutually adjacent positions. Moreover, if the container is placed at the container placement unit, and the bottle is placed at the bottle placement unit, the bottle is preferably positioned at a position which is higher than the container.

In the following, the steps taken for replenishing the container with medicine are described. First, a bottle in which medicine for replenishment is stored is preferably placed at the bottle placement unit. Next, the optical scanner scans a symbol attached to the bottle in which medicine is stored, and at this time, preferably the rotation device rotates the bottle, and the optical scanner scans the symbol attached to the bottle. Then, based on the information obtained from the scanning, the medicine dispensing device determines whether or not the medicine stored in the bottle is the correct medicine for replenishing the container. If the medicine dispensing device determines that the medicine is correct, the medicine dispensing device drives the opening and closing device, and the opening and closing device thereof opens the container. In a preferred embodiment, the medicine dispensing device drives the lock release device, and the lock release device thereof releases a lock of the lid of the container.

After this step, the medicine dispensing device drives the medicine insertion device, and the medicine insertion device thereof inserts the medicine contained in the bottle into the container. At this time, the medicine insertion device preferably tilts the bottle to insert the medicine into the container. More specifically, the medicine dispensing device preferably drives a gripping device, and the gripping device thereof grips and tilts the bottle, and thereby inserts the medicine contained in the bottle into the container. Once the replenishment of the medicine into the container has been completed, the medicine dispensing device preferably drives the camera, and the camera photographs the medicine replenished inside the container. Furthermore, based on the above-mentioned information of the medicine obtained by scanning, the medicine dispensing device preferably obtains a previously prepared image of medicine that should be replenished. The medicine dispensing device also preferably displays the image of the medicine photographed by the camera and the previously prepared image of the medicine on the display device. The user visually compares both images and confirms that the medicine replenished in the container is the correct medicine for replenishment as necessary.

Therefore, according to the embodiments of the present invention a container, which stores medicine and is provided within a medicine dispensing device, is prevented from being replenished with the wrong medicine.

BRIEF DESCRIPTION OF THE DRAWINGS

The present disclosure is described in conjunction with the appended figures:

FIG. 3 is an image of a first step of the first embodiment of the medicine replenishment operation of a medicine dispensing device.

FIG. 4 is an image of a second step of the first embodiment of the medicine replenishment operation of a medicine dispensing device.

FIG. 5 is an image of a third step of the first embodiment of the medicine replenishment operation of a medicine dispensing device.

FIG. 6 is an image of a fourth step of the first embodiment of the medicine replenishment operation of a medicine dispensing device.

FIG. 7 is an image of a fifth step of the first embodiment of the medicine replenishment operation of a medicine dispensing device.

FIG. 8 is an image of a sixth step of the first embodiment of the medicine replenishment operation of a medicine dispensing device.

FIG. 9 is a flow chart showing the operational procedures of the first embodiment of the medicine replenishment operation of a medicine dispensing device.

FIG. 10 is a continuation of the flow chart shown in FIG. 9.

DETAILED DESCRIPTION OF THE INVENTION

§1. Overview of the Medicine Dispensing Device

Figure 1:
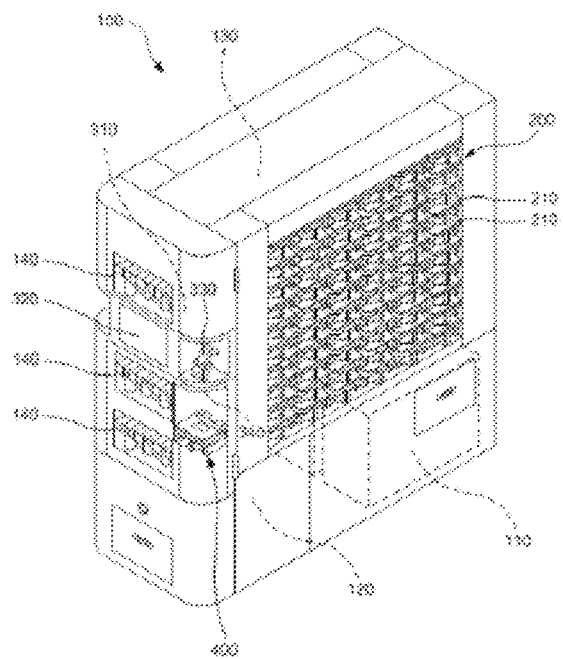
FIG. 1 is a perspective view showing an embodiment of a medicine dispensing device.
Figure 2:
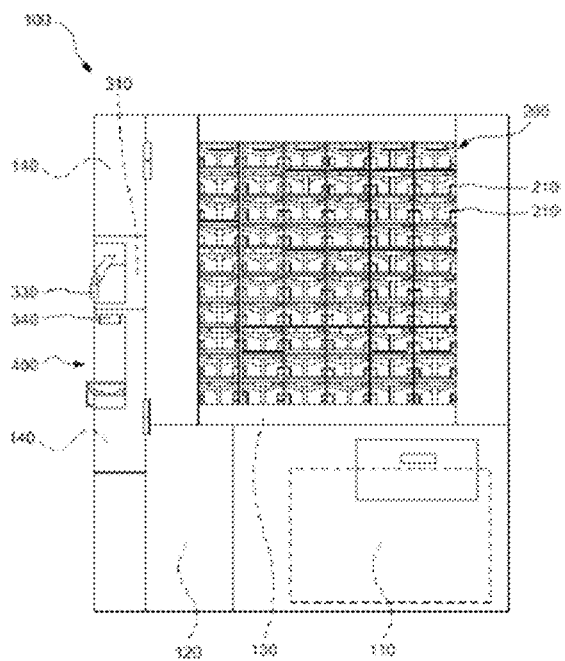
FIG. 2 is a side view of the medicine dispensing device shown in FIG. 1.

FIG. 1 is a perspective view showing an embodiment of the medicine dispensing device, and FIG. 2 is a side view of the medicine dispensing device thereof. The medicine dispensing device 100 shown in these figures is capable of dispensing a prescribed quantity of a prescribed medicine into a vial based on prescription information that has been inputted. The medicine dispensing device 100 thereof has a vial supply device 110, a label attachment device 120, a vial conveyance device 130, and a discharge port 140. The medicine dispensing device 100 further includes a container arrangement unit 200 at a side. Moreover, the medicine dispensing device 100 may include a touch panel display 320, an optical scanner 330, a camera 340, and a medicine replenishing unit 400 at a front surface. The medicine dispensing device 100 further includes an internal control device 310.

The details of the medicine dispensing device 100 thereof are disclosed in International Publication No. 2010/110360, and the details of the medicine dispensing mechanism of the container attached to the container arrangement unit 200 are disclosed in International Publication No. 2013/035692. Accordingly, an overview of the medicine dispensing device 100 is described briefly below.

As shown in FIG. 1 and FIG. 2, the vial supply device 110 is located inside the medicine dispensing device 100 at the bottom rear of the device. The vial supply device 110 thereof functions to store a plurality of vials. The label attachment device 120 is located inside the medicine dispensing device 100 at the bottom front of the device, while the container arrangement unit 200 is provided at both sides at the top side of the medicine dispensing device 100. A plurality of containers (also called cassettes) 210 is arranged linearly in the container arrangement unit 200 thereof. The medicine to be dispensed by the medicine dispensing device 100 is stored in the containers 210 thereof. The vial conveyance device 130 is provided between the container arrangement unit 200 and the container arrangement unit 200, or in other words, is provided at the upper inside of the medicine dispensing device 100. Moreover, a plurality (a quantity of three in the example shown by FIG. 1) of discharge ports 140 is provided at the front surface of the medicine dispensing device 100.

The touch panel display 320 functions both as a display device and an input device. The optical scanner 330 is capable of reading barcodes, two-dimensional codes, or other symbols for optical scanner reading. The camera 340 is provided such that images seen from above the medicine replenishing unit 400 are photographed. Furthermore, the camera 340 is capable of filming both still images and videos. The control device 310 controls operation of each device provided with the medicine dispensing device 100 based on information input from the touch panel display 320 and the like.

When the medicine dispensing device 100 is to dispense medicine, first, the optical scanner 330 scans the symbol attached to the prescription to obtain information on the prescription thereof. Alternatively, if a keyboard and/or a mouse is connected to the medicine dispensing device 100, the medicine dispensing device 100 can receive prescription information input from the keyboard and/or mouse. Furthermore, if the medicine dispensing device 100 is connected to a network, the medicine dispensing device 100 can also receive the input of prescription information via the network.

When the medicine dispensing device 100 receives the input of prescription information, and also receives an input of instructions from a pharmacist to dispense medicine, first, the vial supply device 110 supplies vials to the label attachment device 120. Next, the label attachment device 120 prints a label based on the prescription information that was input, and attaches the label thereof to the vial. Next, the vial conveyance device 130 conveys the vial to which the label was attached to near the container 210 in which the prescribed medicine is stored. The container 210 then dispenses the prescribed quantity of the prescribed medicine into the vial. When the vial is filled with the prescribed medicine, the vial conveyance device 130 conveys the vial to the discharge port 140. A pharmacist, technician, or other person preparing the prescription then retrieves the vial output to the discharge port 140.

Note that if the container 210 is replenished/filled with medicine through procedures of a later-described embodiment, if the person in charge of confirming the image of the medicine that has been replenished/filled has not yet completed the confirmation thereof, or in other words, if there is no record to the effect that confirmation by a person in charge has been completed (see step 230, step 450, and step 650 described below), the medicine dispensing device 100 will not dispense medicine from the container 210. In other words, the medicine dispensing device 100 will only dispense medicine from a container 210 for which a person in charge has confirmed the replenished/filled medicine; that is, the medicine dispensing device 100 will only dispense medicine from a container 210 for which there is a record to the effect that confirmation by a person in charge has been completed.

When the medicine dispensing device 100 dispenses medicine, one of the plural containers 210 becomes empty. When this occurs, the pharmacist must replenish the empty container 210 with new medicine. The present invention has a significant characteristic regarding the replenishment of this medicine. The operation of replenishing the container 210 with new medicine is described in detail below with each embodiment.

§2. First Embodiment of the Medicine Replenishing Operation

A first embodiment of the medicine replenishing operation is described below based on FIG. 3 to FIG. 8. Moreover, the operational procedures of the medicine dispensing device 100 when medicine replenishment is performed are summarized in FIG. 9 and FIG. 10.

Figure 9:
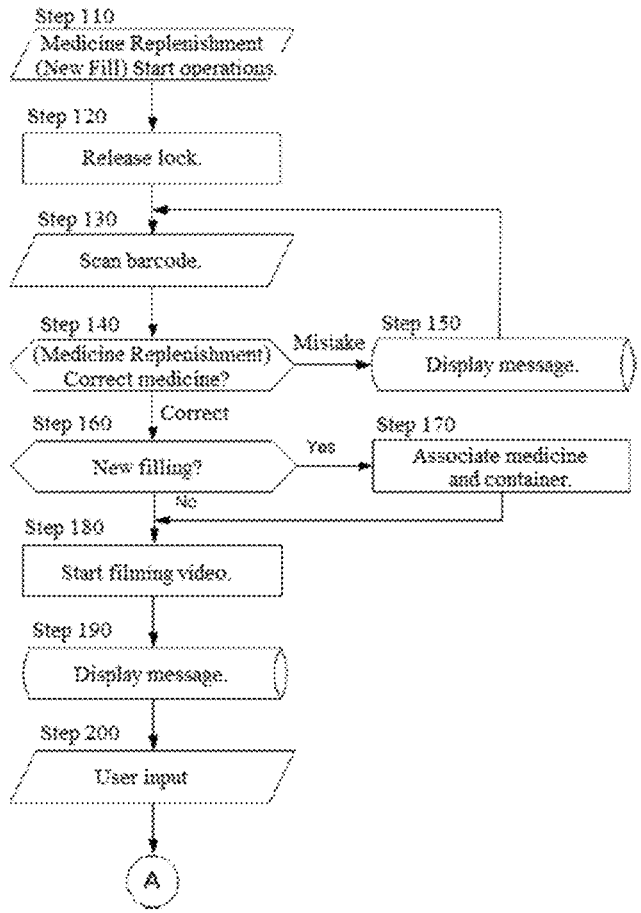

Referring back to FIG. 1, first, the user operates the touch panel display 320, and inputs instructions to start the medicine replenishment operation (step 110 of FIG. 9). While not illustrated, if a container 210 is empty, a red lamp, for example, is lighted. Therefore, with the medicine dispensing device 100, a user can quickly know which container 210 is empty. Furthermore, as shown in FIG. 3, the user retrieves the empty container 210 to be replenished with medicine from the container arrangement unit 200.

In this embodiment, if an unused, empty container 210 is present in the container arrangement unit 200, the user can also fill the empty container 210 with new medicine. In this case, in step 110, the user operates the touch panel display 320 to input instructions to fill the empty container 210 with new medicine. When the medicine dispensing device 100 receives this input, the medicine dispensing device 100 causes a lamp for the unused container 210 to light. The user then retrieves the unused, empty container 210 for which the lamp is lit from the container arrangement unit 200.

The medicine dispensing device 100 of the present embodiment is configured in a way that only a single container 210 can be retrieved from the container arrangement unit 200 at one time. More specifically, the medicine dispensing device 100 has a lock mechanism 201 for preventing retrieval of the container 210 provided at the container arrangement unit 200. Furthermore, if the medicine dispensing device 100 receives input from the user for instructions to start the medicine replenishing operation, the medicine dispensing device 100 drives the lock mechanism 201, and releases the lock of the container to be replenished with medicine (step 120 of FIG. 9). In other words, if the medicine dispensing device 100 receives input from the user with instructions to implement operations to fill with new medicine, the medicine dispensing device 100 releases the lock of the container 210 to be filled with new medicine. Note that the medicine dispensing device 100 maintains the current status of locks of containers 210 other than the container 210 to be replenished or filled. In this manner, the retrieval of an erroneous container 210 from the container arrangement unit 200 by a user can be prevented.

Figures 3, 4, 5:
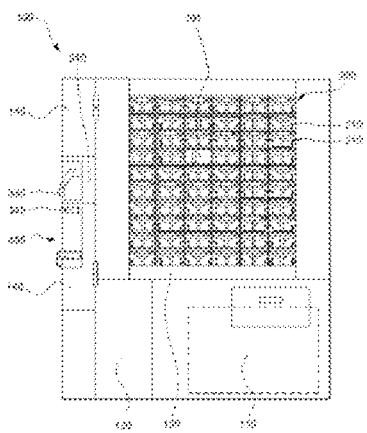
FIG. 3 through FIG. 10 are images used primarily to describe a first embodiment of the medicine replenishment operation of a medicine dispensing device.

As shown in FIG. 4, the user may place the container 210 retrieved from the container arrangement unit 200 on the placement unit 410 of the medicine replenishing unit 400.

Next, the user retrieves a bottle 500 (see FIG. 5), in which the medicine for replenishment or new filling is stored, for example, from a medicine depository or a medicine shelf. Ordinarily, a barcode, two-dimensional code, or other symbol 511 is printed on a label 510 of the bottle 500 in which medicine is stored. The symbol 511 thereof contains information relating to the medicine stored by the bottle 500 thereof. As shown in FIG. 5, the user reads the symbol 511 of the bottle 500 using an optical scanner 330 (step 130 of FIG. 9). Then, based on the scanned results thereof, the medicine dispensing device 100 specifies the medicine entered in the bottle 500.

Next, if the operation this time is to replenish the medicine, the medicine dispensing device 100 determines whether or not the medicine in the bottle 500 is the correct medicine for replenishing the container 210 (step 140 of FIG. 9). If the medicine in the bottle 500 is not the correct medicine for replenishing the container 210, or in other words, if the information specifying the medicine obtained from the symbol 511 differs from the medicine that should be used to replenish the container 210, the medicine dispensing device 100 displays a message on the touch panel display 320 indicating that the medicine in the bottle 500 that was scanned is not the correct medicine for replenishing the container 210 (step 150 of FIG. 9). Moreover, the medicine dispensing device 100 also prompts the user to retrieve the correct medicine. In addition, depending on the settings, the medicine dispensing device 100 may also play a sound to draw the attention of the user. Note that with the present embodiment, the medicine dispensing device 100 is capable of specifying the medicine that should be used to replenish the container 210 based on step 120. More specifically, the medicine dispensing device 100 releases the lock of a specific, single container 210 in step 120 of FIG. 9. The medicine dispensing device 100 maintains information on the medicine that was originally stored in this container 210 on an internal recording device. Accordingly, the medicine dispensing device 100 is capable of specifying the medicine that should be used to replenish the container 210 based on information of the container 210 for which the lock was released in step 120, and on information of the medicine that was stored in this container 210.

Moreover, if new medicine is to be filled in an originally empty container 210 (step 160 of FIG. 9), the medicine dispensing device 100 associates the information of medicine obtained by scanning the symbol 511 in step 130 with the empty container 210 (step 170 of FIG. 9). Furthermore, the medicine dispensing device 100 stores information of medicine to be stored in this container 210 in the internal recording device.

Next, the medicine dispensing device 100 drives the camera 340 to start filming video (step 180 of FIG. 9). In the present embodiment, operations by the user of replenishing or filling the medicine are recorded as video. Furthermore, if a need later arises, a person in charge can replay the video thereof to confirm how the replenishment or filling operations were performed.

The medicine dispensing device 100 also displays instructions on the touch panel display 320 to prompt the user to open a lid 211 of the container 210, and replenish the container 210 with the medicine contained in the bottle 500 (step 190 of FIG. 9). Furthermore, the medicine dispensing device 100 also displays a message on the touch panel display 320 prompting the user, "after medicine replenishment has been completed but prior to closing the lid 211 of the container 210, perform an input with respect to the medicine dispensing device 100 to indicate that replenishment of medicine has been completed."

Figure 6:
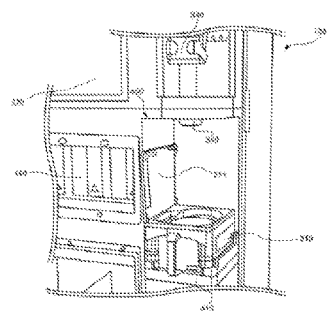
Figure 7:
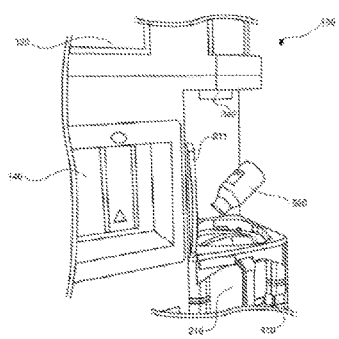

Next, as shown in FIG. 6, the user follows the message displayed on the touch panel display 320, and opens the lid 211 of the container 210, and as shown in FIG. 7, the user then inserts the medicine contained in the bottle 500 into the container 210.

In the next, the user operates the touch panel display 320, and performs an input to indicate that medicine has been inserted into the container 210 (step 200 of FIG. 9). Based on this input, the medicine dispensing device 100 drives the camera 340, and completes the filming of video (see step 180 of FIG. 9), and the camera 340 photographs a still image of the medicine replenished in the container 210 by the user (step 210 of FIG. 10). In another embodiment, the medicine dispensing device 100 may continue filming video, and then take a still image, by cutting the recorded-video, containing a photograph of the medicine inserted into the container 210.

Figure 10:
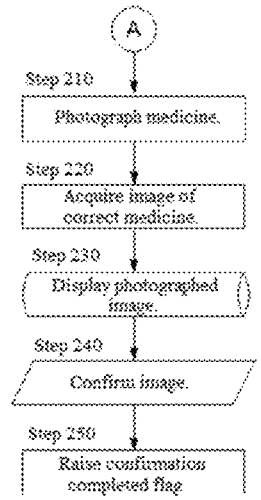

Moreover, the medicine dispensing device 100 acquires an image prepared in advance of the correct medicine that should be used to replenish the container 210 (step 220 of FIG. 10). The medicine dispensing device 100 originally has information regarding medicine stored in the container 210, or in other words, information regarding medicine that should be used to replenish the container 210. Furthermore, the medicine dispensing device 100 stores images of the medicine thereof prepared in advance in an internal recording device. In other words, the medicine dispensing device 100 is capable of acquiring this type of image from a database. Accordingly, the medicine dispensing device 100 can acquire an image prepared in advance of the medicine based on information of the medicine that should be used to replenish the container 210. Note that in an alternative embodiment, the medicine dispensing device 100 may acquire an image of the correct medicine that is to be used to replenish the container 210 based on information of obtained by the optical scanner 330 reading the symbol 511 of the bottle 500 in step 130. Moreover, if an originally empty container 210 is newly filled with medicine, the medicine dispensing device 100 can acquire an image of the medicine that should be used to fill the container 210 based on information of medicine obtained by scanning the symbol 511 in step 130.

Figure 8:
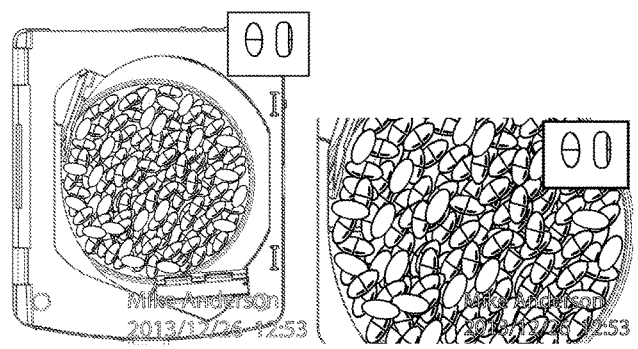

Next, as shown in FIG. 8, the medicine dispensing device 100 displays the image photographed in step 210, or in other words, the image of the medicine that was inserted into the container 210, on the touch panel display 320 (step 230 of FIG. 10). As shown in the image by the left side of FIG. 8, according to the present embodiment, the image is an image as viewed from above the container 210. As shown in this image, the medicine inside the container 210 is photographed. In addition, at the bottom left of the screen, a number which specifies the container is displayed, and at the bottom right of the screen, the name of the person who replenished the container 210 with medicine and the date and time that the image was photographed are displayed. In addition, at the top right of the screen, the medicine dispensing device 100 displays the image obtained in step 200, or in other words, the image prepared in advance of the correct medicine that should be used to replenish the container 210. When the user touches the image displayed on the touch panel display 320, as shown in the image on the right side of FIG. 8, the enlarged image of the photographed medicine is displayed. It should be noted that in this embodiment, the image of the medicine in the container 210 and the image prepared in advance of the medicine that should be used to replenish the container 210 are both simultaneously displayed, but in an alternative embodiment, both images do not have to be displayed on the same screen. For example, the medicine dispensing device 100 may first display the image of the medicine in the container 210 on the touch panel display 320, and then as a next step, the medicine dispensing device 100 may display the image prepared in advance of the correct medicine. Or conversely, the medicine dispensing device 100 may first display on the touch panel display 320 the image prepared in advance of the correct medicine, and then display the image of the medicine in the container 210.

The person in charge then views the images of the medicine displayed on the touch panel display 320, and confirms whether or not the medicine used to replenish the container 210 is the correct medicine for replenishment. Furthermore, if the medicine thereof is correct, the person in charge performs an input to indicate that the medicine in the container 210 is the correct medicine (step 240 of FIG. 10). In other words, the medicine dispensing device 100 receives an input from the person in charge that confirms that the medicine photographed in the image is the correct medicine for replenishing the container 210. In this embodiment, when an image of the medicine inserted in the container 210 and an image prepared in advance of the correct medicine are simultaneously displayed on a single screen, the person in charge can perform a confirmation operation by comparing both images, and therefore the work of the person in charge is simplified. Furthermore, if a container 210, which did not originally store medicine, is newly filled with medicine, the person in charge views the image of the medicine displayed on the touch panel display 320, and confirms whether or not the medicine used to newly fill the container 210 is the correct medicine that should be used to fill the container 210.

Moreover, if the medicine thereof is correct, the person in charge performs an input to indicate that the medicine is correct. In other words, the medicine dispensing device 100 receives an input from the person in charge indicating that the medicine in the photographed image is the correct medicine for filling the new container 210. Note that the confirmation operation of this step can be performed not only immediately after the container 210 is replenished or filled with medicine, but also afterwards, or at a later date. In many cases, the person in charge and the prescription preparer who performs the actual replenishing or filling work differ from the site where the prescriptions are prepared. In this case, there are times when the person in charge can not immediately confirm replenished or filled medicine after the prescription preparer has replenished or filled a container 210 with medicine. The workload of the person in charge is reduced by enabling the confirmation work to be performed later (for example, after the container 210 has been returned to the container arrangement unit 200). Furthermore, when performing confirmation work, the person in charge can, as necessary, view video of the work performed by the prescription preparer to replenish or fill the container 210 with medicine. In other words, if the medicine dispensing device 100 receives input from the user to play video, video of the medicine replenishment or refill work performed by the prescription preparer as recorded in steps 160 to 200 is played on the touch panel display 320.

If the medicine dispensing device 100 receives a confirmation input from the person in charge, information indicating to the effect that a confirmation by the person in charge has been completed is recorded in the recording device of the medicine dispensing device 100 (step 250 of FIG. 10). In other words, the medicine dispensing device 100 raises a flag to indicate that the confirmation by the person in charge has been completed. Lastly, the user closes the lid 211 of the container 210, and returns the container 210 to the original location at the container arrangement unit 200, or in other words, to the location where the container 210 was previously stored. In the present embodiment, if a container 210 does not have a record indicating that confirmation was completed by the person in charge, even if that container 210 is returned to the container arrangement unit 200 for example, the medicine dispensing device 100 will not dispense medicine from that container 210

§3. Second Embodiment of the Medicine Replenishing Operation

A second embodiment of the medicine replenishing operation is described below based on FIG. 11 to FIG. 15. Moreover, the operational procedures of the medicine dispensing device 100 when medicine replenishment is performed are summarized in FIG. 16 and FIG. 17. Explanations of those matters that are common with the matters of the first embodiment are omitted below.

Figures 11, 12, 13:
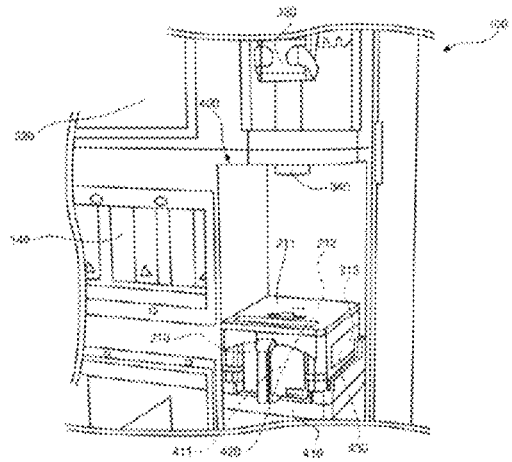
FIG. 11 is an image of a first step of the second embodiment of the medicine replenishment operation of a medicine dispensing device.
FIG. 12 is an image of a second step of the second embodiment of the medicine replenishment operation of a medicine dispensing device.
FIG. 13 is an image of a third step of the second embodiment of the medicine replenishment operation of a medicine dispensing device.

In this embodiment, as shown in FIG. 11, the container 210 is provided with a lock 212, and the lid 211 of the container 210 is capable of locking in a closed state. In other words, when the lid 211 is locked by the lock 212, the lid 211 cannot be opened. When this lock is released, the lid 211 can be opened. Moreover, a lock release device 420 for releasing the lock 212 of the lid 211 is provided at a position corresponding to the lock 212 of the medicine replenishing unit 400.

Furthermore, with the present embodiment, a lock mechanism 411 is provided at the placement unit 410. This lock mechanism 411 is capable of locking the container 210, and when the lock mechanism 411 thereof is operated, the container 210 cannot be retrieved from the placement unit 410.

Moreover, with the container 210 of the present embodiment, an RF (radio frequency) tag 213 is mounted to a side surface opposite the handle (see FIG. 11, the side surface of the depth side). The RF tag 213 thereof is capable of specifying the medicine stored by the container 210. In addition, an RF tag reading device 430, which reads information possessed by the RF tag 213, is provided at a position of the medicine replenishing unit 400 corresponding to the RF tag 213.

First, as shown in FIG. 11, the user places a container 210 retrieved from the container arrangement unit 200 on the placement unit 410 of the medicine replenishing unit 400. When the container 210 is placed on the placement unit 410, the RF tag reading device 430 detects that the RF tag 213 is positioned nearby. Through this, the medicine dispensing device 100 detects that the container 210 has been placed on the placement unit 410 (step 310 of FIG. 16). Furthermore, when the medicine dispensing device 100 detects that the container 210 has been placed on the placement unit 410, the medicine dispensing device 100 drives the lock mechanism 411, and locks the container 210 so that it cannot be removed from the placement unit 410 (step 320 of FIG. 16).

Next, the medicine dispensing device 100 obtains information specifying the container 210 from the RF tag 213. Based on this information, the medicine dispensing device 100 specifies the medicine that should be used to replenish the container 210 (step 330 of FIG. 16). The medicine dispensing device 100 possesses some information, on an internal recording device, about the medicine originally stored in the container 210, or in other words, the medicine that should be used to replenish the container 210. Accordingly, if the medicine dispensing device 100 can specify the container 210, it can also specify the medicine that should be used to replenish the container 210. In an alternative embodiment, the RF tag 213 may contain information of medicine that should be used to replenish the container 210. In this case, the medicine dispensing device 100 can obtain information regarding the medicine that should be used to replenish the container 210 directly from the RF tag 213. In this embodiment, if the medicine that should be used to replenish the container 210 cannot be specified, it is considered that the container 210 is not the container that was originally used. In this case, the medicine dispensing device 100 may further performs other operations, as new operations, to fill the container 210 with medicine.

Figure 16:
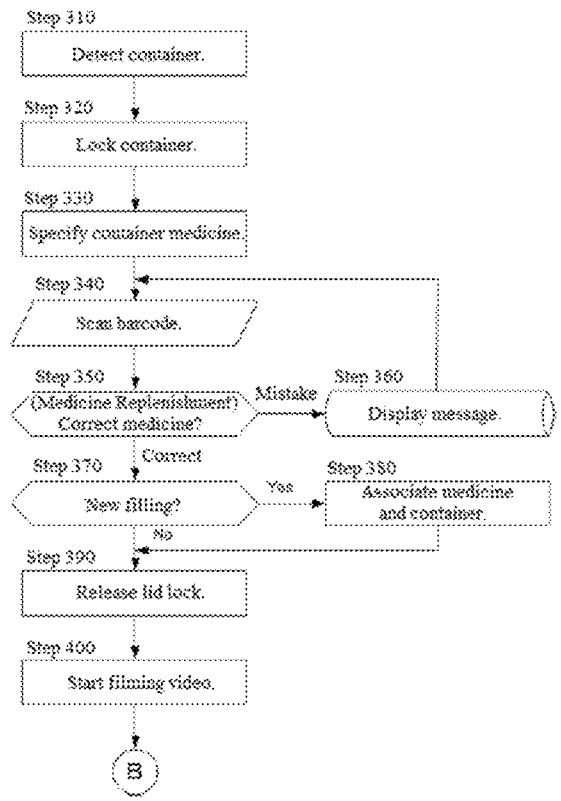
FIG. 16 is a flow chart showing the operational procedures of the second embodiment of the medicine replenishment operation of a medicine dispensing device.

Next, as shown in FIG. 12, the user uses the optical scanner 330 to read the symbol 511 of the label 510 attached to the bottle 500 in which medicine that the user wants to replenish is stored (step 340 of FIG. 16). Based on the scanning results thereof, the medicine dispensing device 100 identifies the medicine contained in the bottle 500.

Next, if the operation this time is to replenish medicine, the medicine dispensing device 100 determines if the medicine contained in the bottle 500 is the correct medicine for replenishing the container 210 (step 350 of FIG. 16). If the medicine contained in the bottle 500 is not the correct medicine for replenishing the container 210, or in other words, if the information specifying the medicine contained in the container 210 differs from the information specifying the medicine acquired from the symbol 511, the medicine dispensing device 100 displays a message on the touch panel display 320 indicating that the medicine contained in the bottle 500 which was scanned is not the correct medicine for replenishing the container 210 (step 360 of FIG. 16).

Furthermore, if an originally empty container 210 is to be newly filled with medicine (step 370 of FIG. 16), the medicine dispensing device 100 associates the medicine information obtained by scanning the symbol 511 in step 340 with the empty container 210 (step 380 of FIG. 16).

If the medicine contained in the bottle 500 is the correct medicine for replenishing the container 210, or in other words, if the information specifying the medicine contained in the container 210 matches the medicine specifying information obtained from the symbol 511, or, if an originally empty container 210 is to be newly filled with medicine, as shown in FIG. 13, the medicine dispensing device 100 drives the lock release device 420, and releases the lock 212 of the lid 211 (step 390 of FIG. 16). Note that in FIG. 13, the container 210 is denoted as a cassette. Furthermore, the medicine dispensing device 100 also drives the camera 340, and starts recording video (step 400 of FIG. 16).

The medicine dispensing device 100 also displays a message on the touch panel display 320, prompting the user to open the lid 211 of the container 210, and to replenish the container 210 with the medicine contained in the bottle 500. Furthermore, the medicine dispensing device 100 also displays a message on the touch panel display 320 prompting the user, "after medicine replenishment has been completed but prior to closing the lid of the container 210, to perform an input with respect to the medicine dispensing device 100 to indicate that replenishment of medicine has been completed" (step 410 of FIG. 17).

Figure 14:
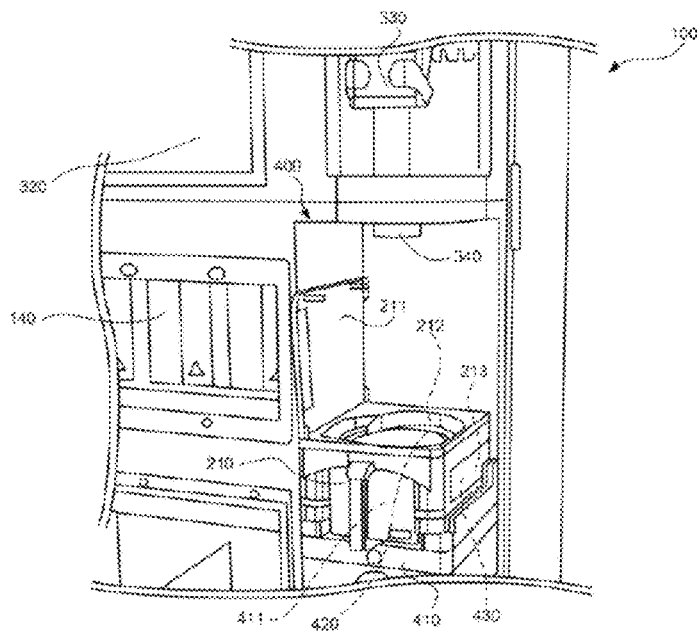
FIG. 14 is an image of a fourth step of the second embodiment of the medicine replenishment operation of a medicine dispensing device.
Figure 15:
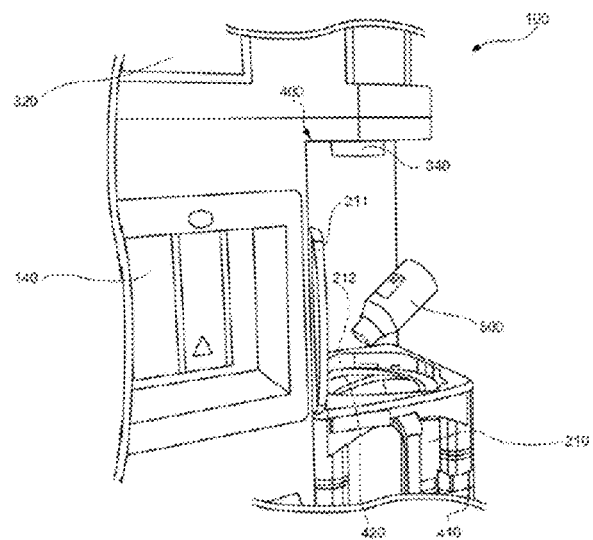
FIG. 15 is an image of a fifth step of the second embodiment of the medicine replenishment operation of a medicine dispensing device.

Next, as shown in FIG. 14, the user follows the message displayed on the touch panel display 320, and opens the lid 211 of the container 210, and then as shown in FIG. 15, the user inserts the medicine contained in the bottle 500 into the container 210.

Figure 17:
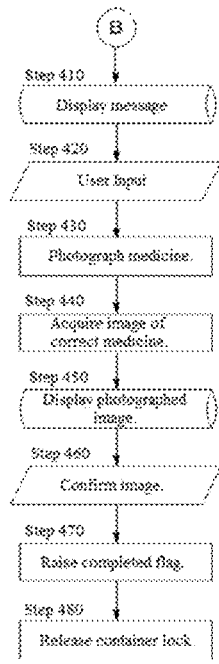
FIG. 17 is a continuation of the flow chart shown in FIG. 16.

In the next step, the user operates the touch panel display 320, and implements an input to indicate that the medicine has been inserted into the container 210 (step 420 of FIG. 17). Based on this input, the medicine dispensing device 100 drives the camera 340, and completes video filming, and then the camera 340 photographs a still image of the medicine that was replenished by the user into the container 210 (step 430 of FIG. 17). The medicine dispensing device 100 also acquires an image prepared in advance of the correct medicine that should be used to replenish the container 210 (step 440 of FIG. 17).

Then, as shown in FIG. 8, the medicine dispensing device 100 displays the image photographed in step 430, or in other words, the image of the medicine inserted into the container 210 on the touch panel display 320 (step 450 of FIG. 17). The person in charge views the image of the medicine displayed on the touch panel display 320, and confirms whether or not the medicine that was used to replenish the inside of the container 210 is the correct medicine for replenishment. If the medicine that was used is correct, the person in charge implements an input to indicate that the medicine was confirmed to be correct (step 460 of FIG. 17). Once the medicine dispensing device 100 receives an input confirmation from the person in charge, information indicating that confirmation by the person in charge has been completed is recorded in the recording device possessed by the medicine dispensing device 100 (step 470 of FIG. 17). Furthermore, the medicine dispensing device 100 drives the lock mechanism 411, and releases the lock of the container 210. Through this, removal of the container 210 from the placement unit 410 is enabled (step 480 of FIG. 17). Note that with this step, even if photographing of the medicine was performed in step 430 but confirmation by the person in charge has not been completed in step 460, the medicine dispensing device 100 will release the lock of the container 210. However, if photographing of the medicine in step 430 has not yet been performed, a message indicating such is displayed on the touch panel display 320, and the medicine dispensing device 100 does not release the lock of the container 210.

Lastly, the user closes the lid 211 of the container 210, and returns the container 210 to its original location in the container arrangement unit 200, or in other words, to the location where the container 210 was previously stored. With the present embodiment as well, the medicine dispensing device 100 will not dispense medicine from a container 210 if there is no record for that container 210 to indicate that a confirmation by the person in charge has been completed.

With the above-described second embodiment, the RF tag 213 was used as the memory medium capable of specifying the medicine to be stored by the container 210. Other embodiments may use a magnetic stripe, a barcode, a two-dimensional code, or the like as the memory medium. Furthermore, in the above-described embodiment, the touch panel display 320 is used as the display device, however, other devices, such as for example, a display, a projector, or the like may be used as the display device.

§4. Third Embodiment of the Medicine Replenishing Operation

Figure 18:
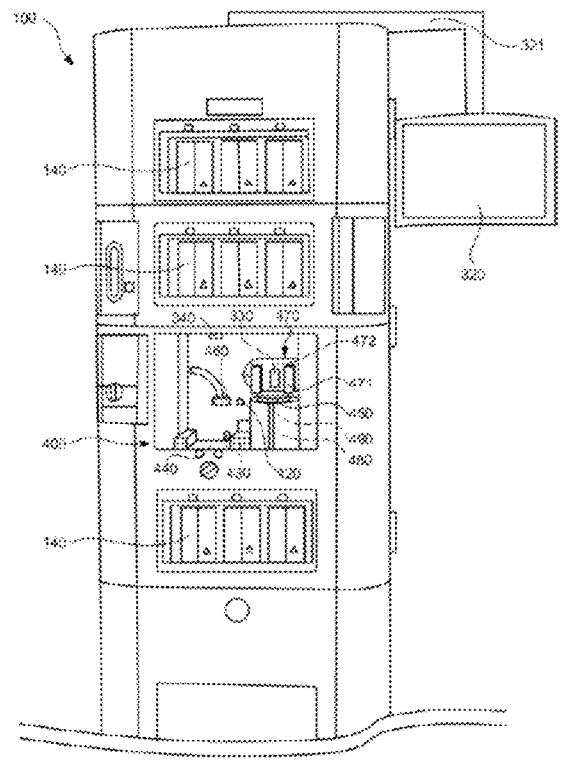
FIG. 18 is a perspective view of a medicine dispensing device of the third embodiment as viewed from the front side.
Figure 19:
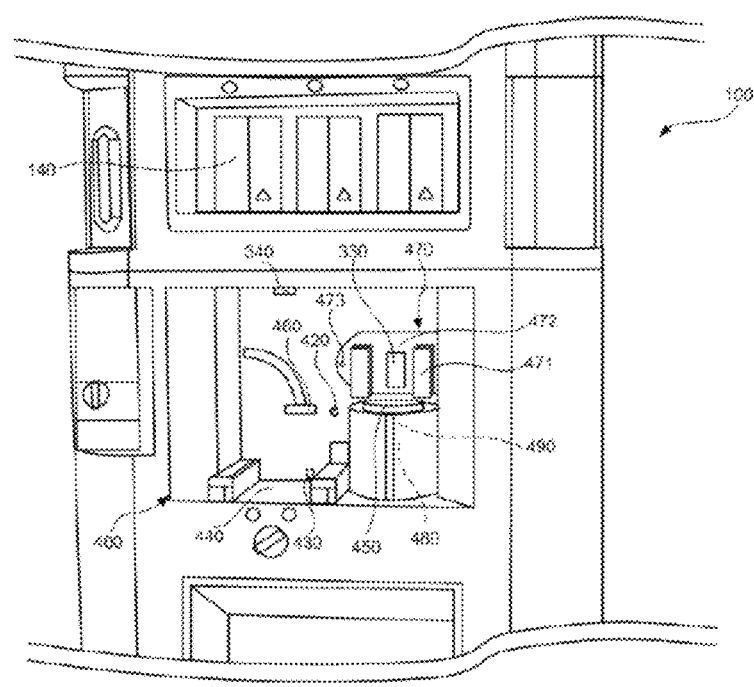
FIG. 19 is an enlarged perspective view near a medicine replenishing unit of the medicine dispensing device shown in FIG. 18.

A third embodiment of the medicine replenishing operation is described below based on FIG. 18 to FIG. 23. The configuration of the medicine dispensing device 100 of this embodiment is shown in FIG. 18 and FIG. 19. Moreover, the operational procedures of the medicine dispensing device 100 when medicine replenishment is performed are summarized in FIG. 24 and FIG. 25. Explanations of those matters that are common with the matters of the second embodiment are omitted below.

Referring next to FIG. 18, a perspective view of the medicine dispensing device 100 according to the third embodiment of the present invention as viewed from the front side is shown. FIG. 19 illustrates an enlarged perspective view of the medicine dispensing device 100 near the medicine replenishing unit 400. In this embodiment, ss shown in FIG. 19, the medicine replenishing unit 400 is provided with a container placement unit 440 and a bottle placement unit 450. The container 210 is placed on the container placement unit 440, and the bottle 500 is placed on the bottle placement unit 450 (see FIG. 21). The container placement unit 440 and the bottle placement unit 450 are provided at mutually adjacent positions, and as shown in FIG. 19, the top surface of the bottle placement unit bottle placement unit 450 is positioned at a higher location than the top surface of the container placement unit 440. Therefore, when a container 210 is placed on the container placement unit 440, and a bottle 500 is placed on the bottle placement unit 450, the bottle 500 is positioned at a location that is higher than the container 210.

The lock release device 420, an opening and closing device 460, and the camera 340 are provided above the container placement unit 440. The lock release device 420 can release the lock of the lid 211 of the container 210, and the opening and closing device 460 can open and close the lid 211 of the container 210.

A rotation device 480 and a weight sensor 490 are provided below the bottle placement unit 450. The weight sensor 490 detects when a bottle 500 is placed on the bottle placement unit 450, and the rotation device 480 rotates the bottle 500. The optical scanner 330 and a medicine insertion device 470 are provided above the bottle placement unit 450. The medicine insertion device 470 can insert medicine contained in the bottle 500 into the container 210, and this medicine insertion device 470 is provided with a gripping device 471 and a bottle transfer device 472. The gripping device 471 is capable of gripping the bottle 500, and the bottle transfer device 472 can rotate the gripping device 471 centered on a rotation axis 473.

In this embodiment, the touch panel display 320 is provided as a separate unit which is different from the medicine dispensing device 100. More specifically, the touch panel display 320 is mounted to the medicine dispensing device 100 via an arm 321.

Figures 20, 21, 22:
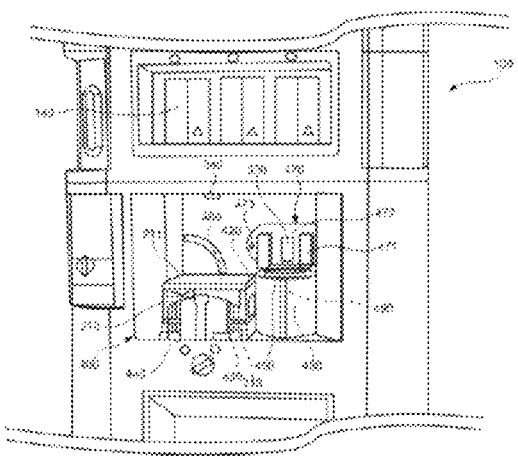
FIG. 20 is an image of a first step of the third embodiment of the medicine replenishment operation of a medicine dispensing device.
FIG. 21 is an image of a second step of the third embodiment of the medicine replenishment operation of a medicine dispensing device.
FIG. 22 is an image of a third step of the third embodiment of the medicine replenishment operation of a medicine dispensing device.

First, as shown in FIG. 20, the user places a container 210 retrieved from the container arrangement unit 200 on the container placement unit 440. By performing this task, the medicine dispensing device 100 detects that a container 210 has been placed on the placement unit 410 (step 510 of FIG. 24). Next, the medicine dispensing device 100 acquires information specifying the container 210 from the RF tag 213. Furthermore, based on this information, the medicine dispensing device 100 also specifies the medicine that should be used to replenish the container 210 (step 520 of FIG. 24). If the medicine to be used to replenish the container 210 cannot be specified, the medicine dispensing device 100 follows another process operation to fill the container 210 with new medicine.

Next, as shown in FIG. 21, the user removes the cap from the bottle 500 in which the medicine to be replenished is stored, and places the bottle 500 on the bottle placement unit 450. When the bottle 500 is placed on the bottle placement unit 450, the weight sensor 490 detects the weight of the bottle 500. Through this, the medicine dispensing device 100 detects the presence of bottle 500 which has been placed on the bottle placement unit 450 (step 530 of FIG. 24).

Then, the medicine dispensing device 100 drives the rotation device 480, and rotates the bottle placement unit 450 (step 540 of FIG. 24), which in turns rotates the bottle 500. Next, the medicine dispensing device 100 reads the symbol 511 of the label 510 attached to the bottle 500 using the optical scanner 330 (step 550 of FIG. 24). In other words, while the rotation device 480 rotates the bottle 500, the optical scanner 330 scans the symbol 511 which is attached to the bottle 500. Accordingly, based on the scan results thereof, the medicine dispensing device 100 specifies the medicine contained in the bottle 500.

Figure 24:
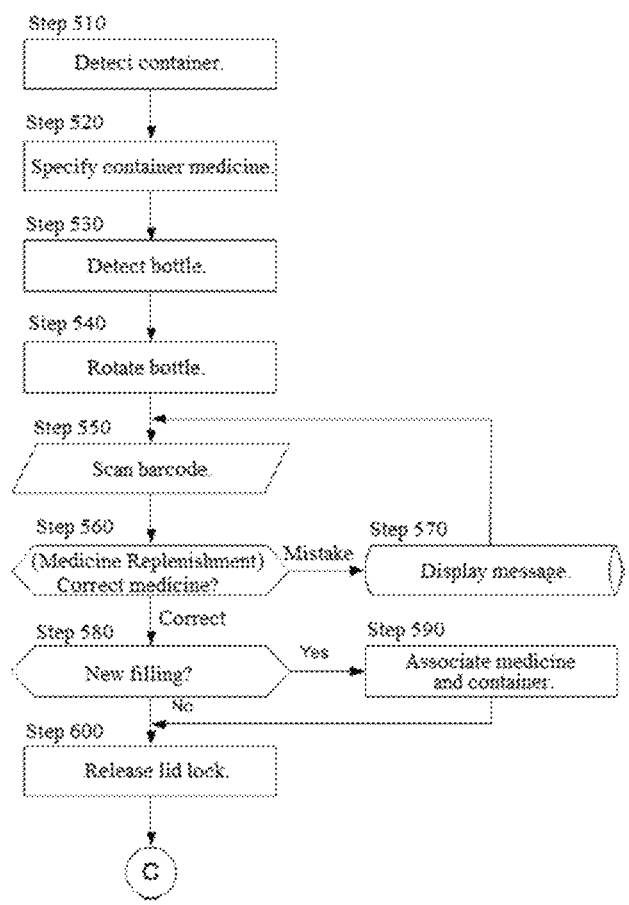
FIG. 24 is a flow chart showing the operational procedures of the third embodiment of the medicine replenishment operation of a medicine dispensing device.

In the next step, the medicine dispensing device 100 determines whether or not the medicine contained in the bottle 500 is the correct medicine for replenishing the container 210 (step 560 of FIG. 24). If the medicine in the bottle 500 is not the correct medicine for replenishing the container 210, or in other words, if the information specifying the medicine contained in the container 210 is different from the information specifying the medicine obtained from the symbol 511, the medicine dispensing device 100 displays a message on the touch panel display 320 indicating that the medicine in the bottle 500, which was scanned previously, is not the correct medicine for replenishing the container 210 (step 570 of FIG. 24).

Moreover, if a new filling has to be performed, meaning medicine is to be filled into a new container 210 which was originally empty (step 580 of FIG. 24), the medicine dispensing device 100 associates information of the medicine obtained by scanning the symbol in step 550 with the empty container 210 (step 590 of FIG. 24).

If the medicine in the bottle 500 is the correct medicine for replenishing the container 210, or in other words, if the information specifying the medicine contained in the container 210 matches the information specifying the medicine acquired from the symbol 511, the medicine dispensing device 100 drives the lock release device 420, and thus releases the lock 212 of the lid 211 (step 600 of FIG. 24). Furthermore, as shown in FIG. 22, the medicine dispensing device 100 drives the opening and closing device 460, for opening the lid 211 of the container 210 (step 610 of FIG. 25)

Figure 23:
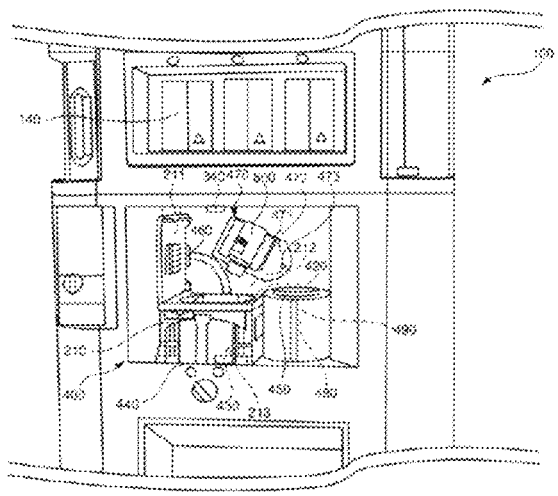
FIG. 23 is an image of a fourth step of the third embodiment of the medicine replenishment operation of a medicine dispensing device.
Figure 25:
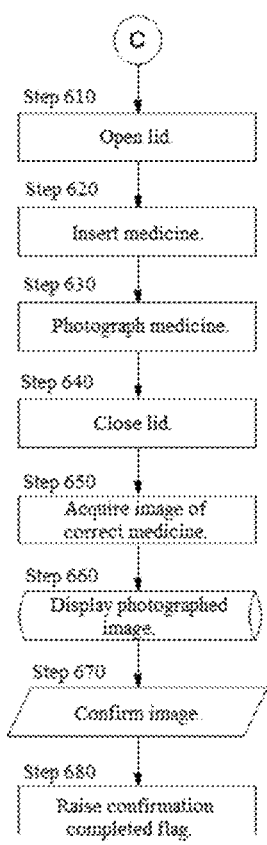
FIG. 25 is a continuation of the flow chart shown in FIG. 24.

Next, as shown in FIG. 23, the medicine dispensing device 100 drives the medicine insertion device 470, to insert medicine from in the bottle 500 into the container 210 (step 620 of FIG. 25). More specifically, the gripping device 471 first grips the bottle 500. Then, the bottle transfer device 472 rotates the gripping device 471 using the rotation axis 473 as the axis of rotation. By doing so, the bottle 500 is placed above the container 210, and the mouth of the bottle 500 is made to face downward. In other words, the bottle 500 is tilted above the container 210, and is made to face obliquely downward. As a result, the medicine falls out of the bottle 500 and enters into the container 210. As with the previous embodiment, when the bottle 500 is placed on the bottle placement unit 450, it is positioned at a location that is higher than the container 210, and when this is done, the bottle 500 can be easily tilted without spilling medicine from the container 210. Once the insertion of medicine into the container 210 has been completed, or in other words, once a prescribed amount of time has passed after insertion is started, the medicine dispensing device 100 drives the bottle transfer device 472, and returns the bottle 500 to its original position, namely on top of the bottle placement unit 450.

In the following step, the medicine dispensing device 100 drives the camera 340, and photographs an image of the medicine replenished in the container 210 (step 630 of FIG. 25). Next, the medicine dispensing device 100 drives the opening and closing device 460, to close the lid 211 of the container 210 (step 640 of FIG. 25). When the lid 211 of the container 210 is closed, the lid 211 is automatically locked. In an alternative embodiment, the medicine dispensing device 100 may drive the lock release device 420, to lock the lid 211. Moreover, the medicine dispensing device 100 acquires an image prepared in advance of the correct medicine for replenishing the container 210 (step 650 of FIG. 25).

Next, as shown in FIG. 8, the medicine dispensing device 100 displays the image photographed in step 630, or in other words, the image of the medicine inserted into the container 210 on the touch panel display 320 (step 660 of FIG. 25). The person in charge views the image of the medicine displayed on the touch panel display 320, and confirms whether or not the medicine that was replenished in the container 210 is the correct medicine for replenishment. If the medicine is correct, the person in charge implements an input that indicates that the medicine is correct (step 670 of FIG. 25). Once the medicine dispensing device 100 receives a confirmation input from the person in charge, indicating that confirmation by the person in charge has been completed, the information is then recorded in the recording device possessed by the medicine dispensing device 100 (step 680 of FIG. 25).

Lastly, the user returns the container 210 to its original location at the container arrangement unit 200, or in other words, to the location where the container 210 was previously stored.

§5. Summary

With the above-described embodiments of the medicine dispensing device 100, when a container 210 that has become empty is to be replenished with medicine, replenishment with the wrong medicine is preferably prevented. Moreover, in the United States, the specification of the medicine dispensing device 100 of the above-described embodiments can be designed with a closed-loop specification. With the closed-loop specification, after medicine has been replenished into the container 210, the visual inspection by the pharmacist of medicine that has been dispensed by the medicine dispensing device 100 based on prescription information can be omitted. In addition, with a closed-loop specification, the medicine dispensing device 100 allows dispensing with the mouth of a vial sealed. In this case, unlike ordinary caps, the user immediately knows when a seal has been broken, and therefore it is easy to determine whether or not a third party has broken the seal of a vial filled with medicine dispensed by the medicine dispensing device 100.

Note that the top surface of the lid 211 of the container 210 has a first region where a label showing information regarding the medicine stored in the container 210 is attached. Additionally, the top surface of the lid 211 of the container 210 has a second region which is adjacent to the first region and is more depressed than the first region. Thus, the first region is uneven, and because it is uneven, the attached label can be easily removed. Accordingly, the work of switching and reattaching a label when the medicine to be stored in the container 210 is different can be smoothly implemented. Further, because the second region is more depressed than the first region, if a label is attached to the first region such that a part of the label covers a part of the second region (such that the label is positioned at an upper part of the second region), a finger or a fingernail can be inserted between the second region and a part of the label, and a portion of the label can be lifted upward from beneath using a finger or a fingernail. Accordingly, the label can be easily peeled off.

Moreover, the container 210 is provided with a main body unit, a first rotating body which rotates with respect to the main body unit, and a second rotating body which rotates with respect to the main body unit. A low friction member for reducing the friction between the second rotating body and the main body unit is positioned at a bottom surface of the second rotating body. The low friction member is inserted into a groove formed in the bottom surface of the second rotating body. With this type of configuration, a separate member for attaching the low friction member (double sided tape for example) is not necessary. Furthermore, because there is not separate member, the second rotating body can be easily washed with water.

While the principles of the disclosure have been described above in connection with specific apparatuses, it is to be clearly understood that this description is made only by way of example and not as limitation on the scope of the invention.

What is claimed is:

1. A medicine dispensing device for dispensing medicine, the medicine dispensing device comprising:
    a container for storing the medicine to be dispensed by the medicine dispensing device;
    a camera capable of photographing the medicine within the container; and
    a display device,
    wherein after the container is replenished with medicine, the camera photographs the replenished medicine in the container,
    the medicine dispensing device displays an image of the medicine photographed by the camera on the display device, and
    the medicine dispensing device is configured to receive an input from a user to confirm that the medicine photographed in the image corresponds to correct medicine, and
    wherein the medicine dispensing device does not dispense medicine from the container in which the medicine was replenished until the input to confirm is received.

2. The medicine dispensing device according to claim 1, wherein the medicine dispensing device acquires the image, which was prepared in advance, of the medicine to be replenished into the container, and
    the medicine dispensing device displays the image of the medicine prepared in advance on the display device.

3. The medicine dispensing device according to claim 1 further comprising an optical scanner, wherein before replenishing the container with medicine:
    the optical scanner scans a symbol attached to a bottle in which the medicine is stored,
    the medicine dispensing device determines whether the medicine stored in the bottle is the correct medicine to be replenished into the container or not based on information obtained from the scan, and
    if the medicine stored in the bottle is not the correct medicine to be replenished into the container, the medicine dispensing device sends a notification informing the user of an error.

4. The medicine dispensing device according to claim 1, wherein the medicine dispensing device further comprises a container arrangement unit having a plurality of containers, in which medicine to be dispensed by the medicine dispensing device is stored, and
    the medicine dispensing device is configured such that only one container is retrieved from the container arrangement unit at a time.

5. The medicine dispensing device according to claim 1 further comprising a camera capable of recording video, wherein the camera records video of an operation of replenishing the container with medicine.

6. A medicine dispensing device for dispensing medicine, the medicine dispensing device comprising:
    a container for storing medicine to be dispensed by the medicine dispensing device, wherein the container is capable of opening and closing;
    an opening and closing device for opening and closing the container;
    a medicine insertion device for inserting medicine into the container; and
    an optical scanner, wherein the optical scanner scans a symbol attached to a bottle in which medicine is stored,
    the medicine dispensing device determines whether the medicine stored in the bottle is correct medicine to be replenished into the container based on information obtained from the scan,
    and if the medicine dispensing device determines that the medicine stored in the bottle is correct medicine, the medicine dispensing device drives the opening and closing device, and the opening and closing device opens the container, and
    subsequently, the medicine dispensing device drives the medicine insertion device, and the medicine insertion device inserts the medicine contained in the bottle in which medicine is stored into the container.

7. The medicine dispensing device according to claim 6, wherein the container is capable of being locked in a closed state,
    the medicine dispensing device further comprises a lock release device for releasing a lock of the container, and
    if the medicine dispensing device determines that medicine stored in the bottle is the correct medicine, the medicine dispensing device drives the lock release device, and the lock release device releases the lock of the container, and
    subsequently, the medicine dispensing device drives the opening and closing device, and the opening and closing device opens the container.

8. The medicine dispensing device according to claim 6 further comprising:
    a container placement unit at which the container to be opened is placed; and
    a bottle placement unit at which a bottle in which the medicine is stored is placed, wherein the container placement unit and the bottle placement unit are provided at mutually adjacent positions.

9. The medicine dispensing unit according to claim 8, wherein when the container is placed at the container placement unit, and the bottle is placed at the bottle placement unit, the bottle is positioned at a position that is higher than that of the container.

10. The medicine dispensing device according to claim 6, wherein the medicine insertion device inserts the medicine into the container by tilting the bottle in which the medicine is stored.

11. The medicine dispensing device according to claim 10, further comprising a gripping device for gripping the bottle in which the medicine is stored, wherein the gripping device grips and tilts the bottle to insert the medicine into the container.

12. The medicine dispensing device according to claim 6 further comprising a rotation device for rotating the bottle in which the medicine is stored, and while the rotation device is rotating the bottle, the optical scanner scans the symbol attached to the bottle.

13. The medicine dispensing device according to claim 6 further comprising a camera capable of photographing the medicine in the container, wherein the camera photographs medicine inserted into the container by the insertion device.

14. The medicine dispensing device according to claim 13 further comprising a display device for:
- displaying an image of the medicine photographed by the camera on the display device,
- acquiring an image of the medicine prepared in advance based on information of the medicine obtained from the scan, and
- displaying the image of the medicine prepared in advance on the display device.

* * * * *